United States Patent [19]

Koyama et al.

[11] Patent Number: 4,557,901
[45] Date of Patent: Dec. 10, 1985

[54] ANALYTICAL ELEMENT

[75] Inventors: Mikio Koyama; Kenichiro Okaniwa; Masakuni Saruhashi; Yuko Ohmachi, all of Hino, Japan

[73] Assignee: Konishiroku Photo Industry Co., Ltd., Tokyo, Japan

[21] Appl. No.: 437,691

[22] Filed: Oct. 29, 1982

[30] Foreign Application Priority Data

Nov. 4, 1981 [JP] Japan ................................ 56-177596

[51] Int. Cl.$^4$ ...................... G01N 33/52; G01N 21/78
[52] U.S. Cl. ........................................ 422/56; 422/57; 435/805
[58] Field of Search .................... 436/66, 94, 904, 170; 435/28, 805, 14; 422/56, 57

[56] References Cited

U.S. PATENT DOCUMENTS 4,283,491 8/1981 Dappen ............................ 422/56 X
4,312,834 1/1982 Vogel et al. .......................... 422/56
4,372,746 2/1983 Habenstein ...................... 422/56 X
4,390,343 6/1983 Walter .............................. 422/56 X Primary Examiner—Arnold Turk
Attorney, Agent, or Firm—Frishauf, Holtz, Goodman & Woodward

[57] ABSTRACT

An analytical element for use in analysis of a component in an aqueous fluid, comprising
 (a) a light-transmissive support;
 (b) a reagent layer; and
 (c) a porous spreading layer,
being characterized in that the reagent layer contains a substantially water-dispersible copolymer obtained by copolymerization of at least one copolymerizable monomer, which is water soluble and has a nonionizable group in the side chain, with at least one copolymerizable hydrophobic monomer.

The analytical element of this invention is good with less formation of fogging, higher in color forming density and indicating higher sensitivity.

13 Claims, No Drawings

ANALYTICAL ELEMENT

This invention relates to an analytical element for analysis of a component in an aqueous fluid. More particularly, it pertains to an improved analytical element for analysis of a component in a biological fluid.

BACKGROUND OF THE INVENTION

In the prior art, developments have been made of analytical elements for detection of specific biochemical substances present in body fluids and they have been used for clinical tests and others. These are based on utilization of the phenomenon of coloration of a reagent impregnated in the analytical element with a substance to be detected. Recently, use is made widely of analytical elements comprising filter papers, etc. impregnated with reagents.

For example, U.S. Pat. No. 3,050,373 or No. 3,061,523 discloses preparation of an analytical element by impregnating a fibrous porous layer such as a filter paper with a reagent layer, followed by drying. Further, various attempts have been made to avoid interferences in detection with the use of such an element.

For example, as disclosed in Japsnese Patent Publication No. 39558/1975, a filter paper impregnated with a reagent solution and dried is further impregnated with a solution such as of ethyl cellulose and dried to be coated with a semipermeable film, for the purpose of suppressing excessive adhesion of a liquid sample or controlling water retention. Alternatively, as disclosed in Japanese Patent Publication No. 6551/1978, a net of fine mesh such as a fabric or a web is covered on a filter paper impregnated with a reagent for protection from contamination such as by hand contact.

These analytical elements are easy in handling and can give immediate results. However, since uneven coloration of analytical elements may frequently be caused whereby analytical results may be varied, they are inferior in quantitative characteristic. As a consequence, they are useful only for qualitative or semiquantitative analysis. This is because, in preparation of a fibrous porous layer such as filter paper, it is in the first place difficult to obtain a product of uniform structure, and hence no uniform analysis of a reagent is usually possible on impregnation with the reagent. Further, so called chromatographic phenomenon may also occur when using such a fibrous filter paper, whereby excessive ununiform migration of the sample component to be analyzed or the reaction reagent may occur in the reagent layer to bring about localized higher concentrations of such components in the layer.

As improvements over the drawbacks of the analytical test strip of the prior art, which have also improved dramatically the quantitative characteristic thereof, there are known multi-layer analytical elements as disclosed in, for example, Japanese Patent Publication No. 21677/1978 and Japanese Provisional Patent Publication No. 24576/1981.

However, the above analytical elements also suffer from serious deterioration of various reagents contained in the reagent layers during the period of storage, thus giving marked disadvantages with respect to precision and reliability of the analyses. There was caused by deterioration of the activity of peroxidase contained in the analytical element which will exhibit catalytic activity for oxidation of an indicating composition, because the material constituting the analytical element is permeable to an aqueous fluid and therefore greatly influenced by the air and water.

Accordingly, formation of a detectable product which is proportional correctly and without contradiction to the concentration of a component in an aqueous fluid is obstructed.

Further, when an aqueous fluid which is the sample to be tested is applied to the aforesaid analytical element, a large amount of an aqueous fluid per unit area is contained in a reagent layer comprising a hydrophilic colloidal substance, and said element is incubated at a temperature of room temperature or higher. As a result, at the aqueous fluid absorbing portion of the reagent layer in the analytical element, there occurs undesirable swelling or dissolution of the hydrophilic colloidal substance of said layer, whereby no uniform color formation can be expected because of migration of the detectable substance, namely marked increase of the chromatographic phenomenon.

A proposal to improve the above drawback is described in detail in Japanese Provisional Patent Publication No. 50393/1979. That is, storability of a reagent, especially peroxidase is stated to be markedly improved by addition of a water-dispersible polymer comprising a copolymer of anionic monomers, namely a polymer latex to said reagent layer.

However, the above polymer latex is known to interact strongly with gelatin, thereby causing frequently agglomeration during preparation of a coating solution.

As other drawbacks, anionic monomers are difficult incorporate into latex particles and this method has also the disadvantage in preparation to cause agglomeration during preparation of the copolymer.

The present inventors have made extensive studies to overcome the above drawbacks.

The first object of this invention is to provide an analytical element improved in storability of a reagent. The second object of this invention is to provide an analytical element which enables quantitative and simple measurement without requiring any skilled operational procedure.

SUMMARY OF THE INVENTION

Such objects and other objects as hereinafter described of this invention are achieved in an analytical element for use in analysis of a component in an aqueous fluid, constituted of:
(a) a light-transmissive support;
(b) a reagent layer comprising one layer or a plurality of layers, positioned on one side of said support, said reagent layer containing at least one reagent reactive with the component in the aqueous fluid and comprising a hydrophilic colloidal substance; and
(c) a porous spreading layer comprising one layer or a plurality of layers, positioned on said reagent layer on the side opposite to that of said support,
by incorporating in said reagent layer a substantially water-dispersible copolymer obtained by copolymerization of at least one copolymerizable monomer, which is water soluble and has a non-ionizable group in the side chain, with at least one copolymerizable hydrophobic monomer.

DETAILED DESCRIPTION OF THE INVENTION

The copolymerizable monomer to be used in this invention which is water-soluble and has a non-ionizable group in the side chain (hereinafter referred to merely as non-ionizable monomer) may preferably a compound represented by the following formula [I]:

Formula:

$$CH_2=\underset{R_2}{\overset{R_1}{C}}-COX+CHCH_2O)_{\overline{n}}R_3 \quad [I]$$

wherein $R_1$ and $R_2$ may be the same or different a hydrogen atom or a methyl group, respectively, $R_3$ is a hydrogen atom or a mono-valent organic residue, X is an oxygen atom or a di-valent organic group represented by the formula $$-\underset{R_4}{N}-,$$

where $R_4$ is a hydrogen atom, an alkyl group or a group represented by the formula:

$$+CHCH_2O)_{\overline{m}}R_3,$$
$$\quad\; R_2$$

and n and m are each integers of 2 to 100.

Typical examples of non-ionizable monomers of this invention are shown below, but this invention is not limited thereto.

EXEMPLARY MONOMERS $CH_2=CHCOO+CH_2CH_2O)_{\overline{3}}H$ (1)

$CH_2=CHCOO+CH_2CH_2O)_{\overline{4}}H$ (2)

$CH_2=CHCOO+CH_2CH_2O)_{\overline{5}}H$ (3)

$CH_2=CHCOO+CH_2CH_2O)_{\overline{25}}H$ (4)

$CH_2=CHCOO+CH_2CH_2O)_{\overline{10}}CH_3$ (5)

$CH_2=CHCOO+CH_2CH_2O)_{\overline{8}}CH_2CH_2CH_2CH_3$ (6)

$CH_2=CHCOO+CH_2CH_2O)_{\overline{20}}$—⌬ (7)

$CH_2=\underset{CH_3}{\overset{|}{C}}COO+CH_2CH_2O)_{\overline{5}}H$ (8)

$CH_2=\underset{CH_3}{\overset{|}{C}}COO+CH_2CH_2O)_{\overline{3}}H$ (9)

$CH_2=\underset{CH_3}{\overset{|}{C}}COO+CH_2CH_2O)_{\overline{30}}H$ (10)

$CH_2=\underset{CH_3}{\overset{|}{C}}COO+CH_2CH_2O)_{\overline{15}}CH_2CH_3$ (11)

$CH_2=\underset{CH_3}{\overset{|}{C}}COO+CH_2CH_2O)_{\overline{20}}$—⌬ (12)

$CH_2=CHCOO+CHCH_2O)_{\overline{5}}H$
$\qquad\qquad\quad\; |$
$\qquad\qquad\quad\; CH_3$ (13)

$CH_2=CHCOO+CHCH_2O)_{\overline{10}}H$
$\qquad\qquad\quad\; |$
$\qquad\qquad\quad\; CH_3$ (14)

$CH_2=CHCOO+CHCH_2O)_{\overline{5}}$—⌬
$\qquad\qquad\quad\; |$
$\qquad\qquad\quad\; CH_3$ (15)

$CH_2=\underset{CH_3}{\overset{|}{C}}COO+\underset{CH_3}{\overset{|}{C}HCH_2O})_{\overline{10}}H$ (16)

$CH_2=\underset{CH_3}{\overset{|}{C}}COO+\underset{CH_3}{\overset{|}{C}HCH_2O})_{\overline{15}}H$ (17)

$CH_2=\underset{CH_3}{\overset{|}{C}}COO+\underset{CH_3}{\overset{|}{C}HCH_2O})_{\overline{20}}CH_2CH_2CH_3$ (18)

$CH_2=CHCONH+CH_2O)_{\overline{10}}H$ (19)

$CH_2=CHCONH+CH_2CH_2O)_{\overline{15}}H$ (20)

$CH_2=CHCONH+CH_2CH_2O)_{\overline{5}}CH_3$ (21)

$CH_2=CHCON+CH_2CH_2O)_{\overline{5}}H$
$\qquad\qquad\; |$
$\qquad\qquad\; +CH_2CH_2O)_{\overline{3}}H$ (22)

$CH_2=\underset{CH_3}{\overset{|}{C}}CONH+CH_2CH_2O)_{\overline{15}}H$ (23)

$CH_2=\underset{CH_3}{\overset{|}{C}}CONH+CH_2CH_2O)_{\overline{21}}CH_3$ (24)

$CH_2=\underset{CH_3}{\overset{|}{C}}-CONH+\underset{CH_3}{\overset{|}{C}HCH_2O})_{\overline{30}}H$ (25)

The other vinyl monomer to be used in this invention may be any monomers having hydrophobicity and being capable of radical polymerization, whether it may be a single monomer or a combination of two or more monomers. It is also possible to copolymerize a hydrophilic monomer such as acrylic acid with a hydrophobic vinyl monomer.

As the vinyl monomer, there may preferably be employed a copolymerizable ethylenically unsaturated nitrile; a styrene; an acrylate; a methacrylate; an acrylamide; a methacrylamide; a vinyl heterocyclic compound; a crosslinkable monomer; a vinyl halide; a vinylidene halide; a vinyl ester; a vinyl ether; and a conjugated diene.

As a copolymerizable ethylenically unsaturated nitrile, there may be included, for example, acrylonitrile, methacrylonitrile, and α-chloroacrylonitrile.

As a styrene, there may be mentioned, for example, styrene, p-methylstyrene, α-methylstyrene, p-chlorostyrene, and chloromethyl styrene.

Examples of an acrylate are methyl acrylate, ethyl acrylate, n-propyl acrylate, n-butyl acrylate, isobutyl acrylate, sec-butyl acrylate, 2-hydroxyethyl acrylate and 2-hydroxypropyl acrylate.

Examples of a methacrylate are methyl methacrylate, ethyl methacrylate, n-butyl methacrylate, 2-hydroxyethyl methacrylate and 2-hydroxypropyl methacrylate.

An acrylamide may be exemplified by acrylamide, diacetoneacrylamide, methylolacrylamide and methylacrylamide.

An methacrylamide may be exemplified by methacrylamide and benzylmethacrylamide.

A vinyl heterocyclic compound may include N-vinylpyrrolidone, N-vinylimidazole, vinylpyridines (e.g. 4-vinylpyridine, 2-vinylpyridine, etc.).

As a crosslinkable monomer, there are, for example, divinyl benzene, ethyleneglycol dimethacrylate, trimethylolpropane triacrylate, and pentaerythritol trimethacrylate.

As a vinyl halide, vinyl chloride and vinyl fluoride are typically used.

As a vinylidene halide, vinylidene chloride and vinylidene fluoride are typically used.

Typical examples of a vinyl ester may be vinyl acetate, vinyl butyrate, etc.

A vinyl ether may be exemplified typically by vinyl methyl ketone, and a conjugated diene by 1,3-butadiene, isoprene, 2,3-dimethyl-1,3-butadiene, etc.

As described above, various copolymerizable vinyl monomers can be used in this invention. The non-ionizable monomer according to this invention represented by the formula [I] can be used in an amount of about 0.5 to about 30% by weight, preferably about 1.0 to about 20% by weight. The copolymerizable hydrophobic vinyl monomer may be used in an amount of about 70 to about 99.5% by weight, preferably about 80 to about 99% by weight.

Typical examples of the water-dispersible copolymer of this invention are enumerated below, but this invention is not limited thereto.

EXEMPLARY COPOLYMERS

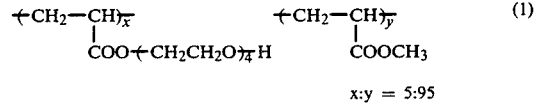

$x{:}y = 5{:}95$      (1)

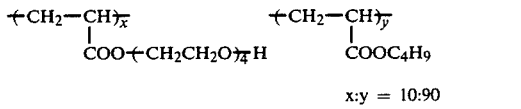

$x{:}y = 10{:}90$      (2)

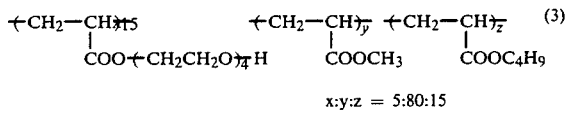

$x{:}y{:}z = 5{:}80{:}15$      (3)

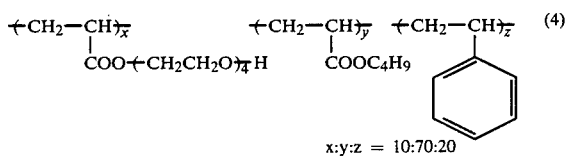

$x{:}y{:}z = 10{:}70{:}20$      (4)

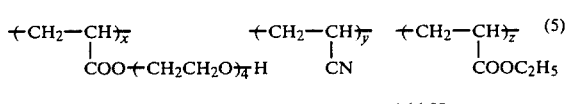

$x{:}y{:}z = 4{:}16{:}80$      (5)

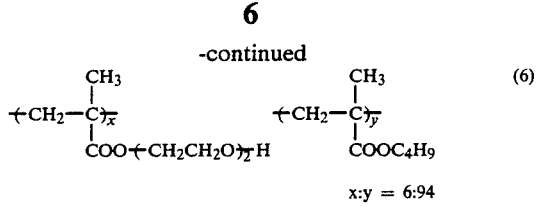

$x{:}y = 6{:}94$      (6)

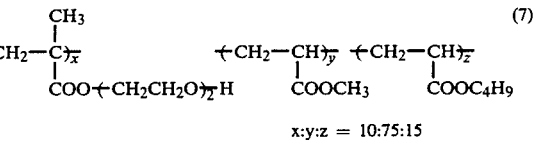

$x{:}y{:}z = 10{:}75{:}15$      (7)

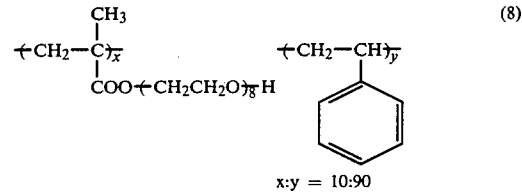

$x{:}y = 10{:}90$      (8)

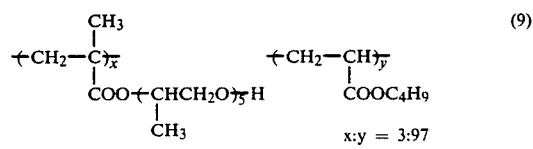

$x{:}y = 3{:}97$      (9)

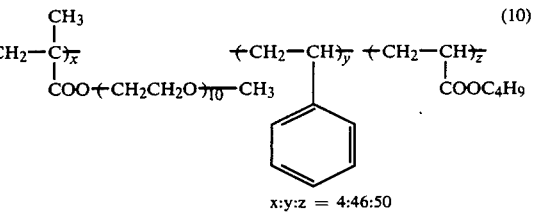

$x{:}y{:}z = 4{:}46{:}50$      (10)

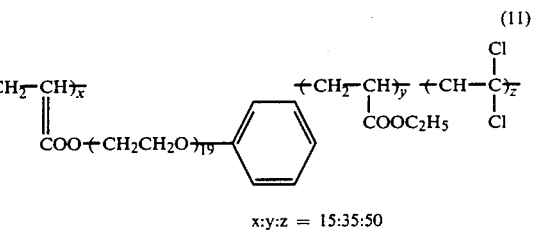

$x{:}y{:}z = 15{:}35{:}50$      (11)

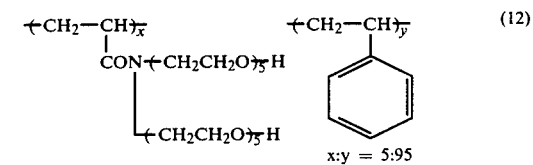

$x{:}y = 5{:}95$      (12)

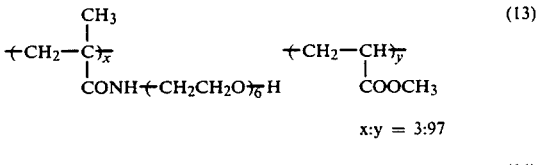

$x{:}y = 3{:}97$      (13)

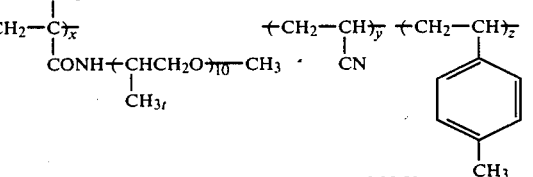

$x{:}y{:}z = 15{:}35{:}50$      (14)

-continued

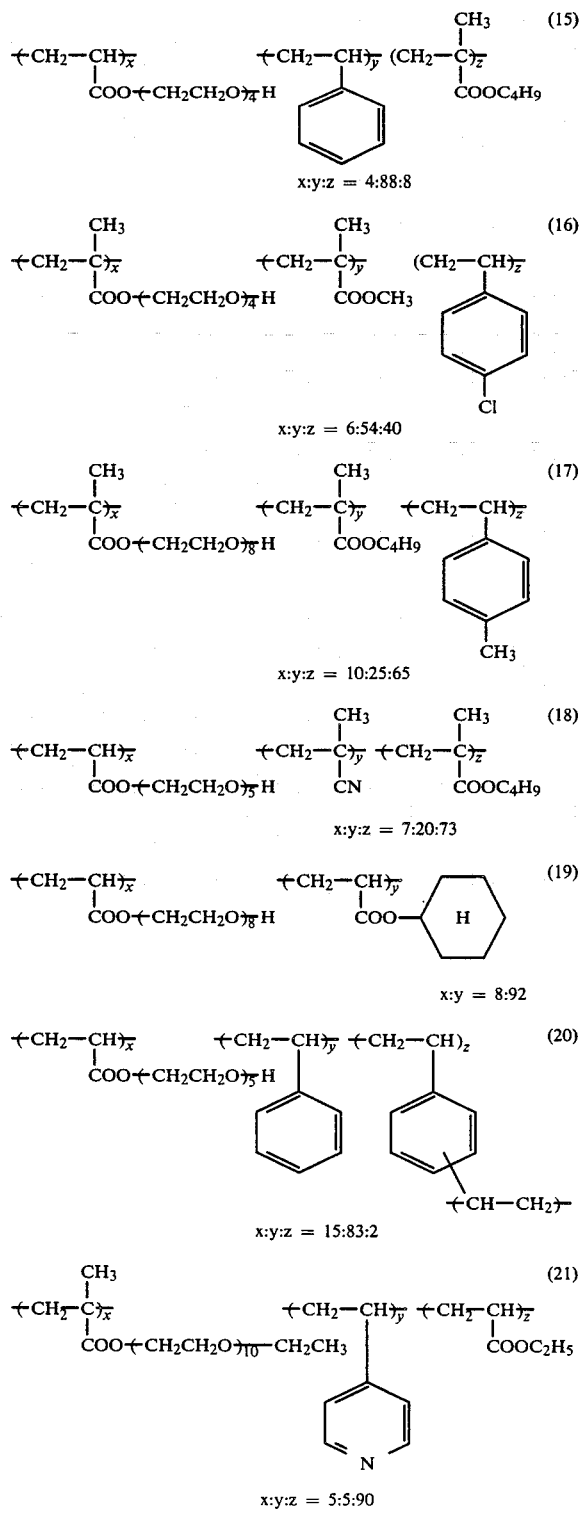

The water-dispersible copolymer according to this invention can be synthesized as mentioned above by conventional emulsion polymerization techniques with a water-soluble radical polymerization initiator by using the non-ionizable monomer of this invention and a vinyl monomer together with a surfactant.

It is also possible to synthesize a water-dispersible copolymer according to the so called no emulsifier emulsion polymerization technique, without use of a surfactant, with a water-soluble radical polymerization initiator from the non-ionizable monomer of this invention and a vinyl monomer.

The following Synthesis examples are set forth for illustration of the water-dispersible copolymer according to this invention, but they are not limitative of this invention.

SYNTHESIS EXAMPLE 1 [SYNTHESIS OF EXEMPLARY COPOLYMER (1)]

In a one-liter four-necked flask equipped with a stirring means, a cooling tube, a thermometer and a tube for introduction of nitrogen, there were charged 500 ml and degassed deionized water, 5.0 ml of Trax H-45 (produced by Nippon Oil and Fats Co., effective ingredient: 30%) and 7.5 g of Exemplary monomer (2), and the mixture was stirred at a stirring speed of 250 rpm under nitrogen stream at room temperature for one hour. Then, the inner temperature was allowed to be elevated to 45° C., whereupon 142.5 g of methyl acrylate was added simultaneously with the addition of an aqueous solution of 0.4 g of potassium persulfate and 0.3 g of sodium methabisulfite each being dissolved in 20 ml of degassed deionized water.

The reaction was thereafter allowed to proceed at an inner temperature of 45° C. for 3 hours, further at an inner temperature elevated to 60° C. for 3 hours. After completion of the reaction, the inner temperature was cooled to room temperature and the contents were subjected to filtration to obtain a milky white latex.

Conversion: 99.7%

Viscosity: 2.4 cp (as measured by B-type viscometer)

SYNTHESIS EXAMPLE 2 [SYNTHESIS OF EXEMPLARY COPOLYMER (15)]

In a one-liter four-necked flask equipped with a stirring means, a cooling tube, a thermometer and a tube for introducing nitrogen, there were charged 500 ml of degassed deionized water and 6 g of Exemplary monomer (2), and the mixture was stirred until a homogeneous mixture was obtained. Then, 132.0 g of styrene and 12 g of n-butyl methacrylate were added and the mixture was stirred at a stirring speed of 300 rpm under a nitrogen stream at room temperature.

Then, the inner temperature was allowed to be elevated to 60° C., whereupon aqueous solutions of 0.4 g of potassium persulfate and 0.3 g of sodium methabisulfite each being dissolved in 20 ml of degassed deionized water were added at the same time. The reaction was thereafter allowed to proceed at an inner temperature of 60° C. at a stirring speed of 300 rpm under a nitrogen stream for 8 hours.

After completion of the reaction, the inner temperature was cooled to room temperature and the contents were subjected to filtration to obtain a milky white latex.

Conversion: 99.3%

Viscosity: 2.4 cp (as measured by B-type viscometer)

The thus prepared water-dispersible copolymer may be used as such or alternatively may of course be used after purification by removal of monomers remaining in trace amounts by means of dialysis, ultrafiltration, etc.

The light-transmissive support of this invention (hereinafter referred to as the support of this invention) may be any kind of support. It is preferred that the support is impervious to liquid. The specific materials to be used as the support are not critical and there may be included for the purpose of this invention various polymeric materials, as exemplified by cellulose acetate, polyethyleneterephthalate, polycarbonate or polystyrene. The support may have a thickness which may optionally be determined, but typically a thickness of about 50 microns to 250 microns.

The reagent layer according to this invention can be coated directly on the support of this invention but it is also possible in some cases to enhance adhesion between the reagent layer and the support by employment of a light-transmissive subbing layer. The reagent layer is provided for the purpose of incorporating a reagent which can react with a component to be analyzed to form a detectable reaction product.

A coated product is preferred, which contains one or more kinds of reagents dispersed or dissolved as binder in a hydrophilic colloidal substance. As the hydrophilic colloidal substance, a natural or synthetic substance is preferred. More preferably, there may be included polysaccharides or synthetic hydrophilic substances, such as gelatin, gelatin derivatives, hydrophilic cellulose derivatives, dextran, gum arabic and agarose, etc.; water soluble polyvinyl compounds such as polyvinyl alcohol and polyvinylpyrrolidone; and water soluble acrylamide polymers. These materials may be sometimes chosen depending partially on the optical properties of a detectable product.

The water-dispersible copolymer of this invention may be added to the hydrophilic colloidal substance in said reagent layer or partially replace said substance to achieve the obove object. These water-dispersible copolymers of this invention may be incorporated in an amount of about 5 to about 60% of the total binder, more preferably about 15 to about 50%.

In this way, the above object and other objects can be accomplished. As one of the other objects, there is alleviation of curling of the coated film and, as still another object, there is improvement of dimensional stability of the coated film.

The above objects are well known in the art of photographic industry, but they can also impart higher reliability of analysis to the technique in the field of multilayer analytical elements.

Further, as an unexpected effect, there may be mentioned an increased difference in color formed densities between certain analyte concentration and others. An increase of difference in color formed densities between certain different analyte concentrations in analytical reaction is of course very advantageous, since it leads to an improvement in detection sensitivity.

The analytical element of this invention can be constituted easily by suitable selection of test reagents in said reagent layer as described above so as to be available for analysis of blood components, such as glucose, albumin, urea nitrogen, bilirubin, ammonia, uric acid, cholesterol, triglyceride, glutamateoxaloacetate transaminase, glutamate-pyruvate transminase, lactic acid dehydrogenase, lactic acid, creatinine, amylase, chloride, calcium, etc. as well as a number of other components.

Addition of the water-dispersible copolymer of this invention is effective for improvement of storability of these test reagents. As a particularly preferred example, there may be mentioned an appropriate enzyme exhibiting a catalytic activity for oxidation of a predetermined component, indicating compositions which can produce detectable products through the reaction with a peroxidase in the presence of a peroxidase and compounds for pH control. German Provisional Patent Publication No. 2735690 discloses a great number of examples. As a typical example of such reagents, there is a reagent for analysis of glucose comprising a phosphate buffer system of pH 6 containing glucose oxidase, peroxidase, 7-hydroxy-1-naphthol and 4-aminoantipyrine hydrochloride.

The porous development layer for formation of a multilayer analytical element with the above reagent layer may also have a spreading layer, light-reflective layer, varrier layer, subbing layer, filtering layer or registration layer, as disclosed in U.S. Pat. Nos. 3,929,158 and No. 4,042,335.

These are coated on the reagent layer as described above as a dispersion in the form of a slurry of cellulose diacetate in the co-presence of a good solvent and a poor solvent in various white pigments, as described in the above patents, whereby there is obtained a so called non-fibrous porous spreading layer having formed a layer with a predetermined pore size and a high void volume. As the same kind as this product, a microfilter known under the trade name of Milliporefilter is of course useful.

On the other hand, it is also possible to use fibrous spreading layers as disclosed in Japanese Provisional Patent Publication No. 24576/1981. Further, fibrous spreading layers as disclosed in Japanese Patent Applications No. 13203/1981 and No. 65466/1981 are also useful.

These layers have the three functions, namely:
(1) To distribute a constant volume of a fluid sample uniformly to a constant volume per unit area through the reagent layer;
(2) To remove substances or factors which interfere with the analytical reactions in the fluid sample; and
(3) To effect a background action which reflects the measured light transmitted through the support during spectrophotometric analysis.

These three functions may be performed separately in different layers or alternatively all in one layer, as desired, depending on the cases. Further, for example, it is also possible to use a combination of a layer having only a reflective background function among said functions with another layer having the other two functions.

The fluid sample to be used in this invention may be an aqueous solution, typically a biological fluid sample such as blood, lymph, urine, etc. As the blood, either one containing blood cell components (erythrocytes, leucocytes, platelets, etc.) generally called whole blood or blood plasma or blood serum removed of these components may be available.

The fluid sample may be used in an analysis in an amount depending on the purpose of analysis, but preferably in an amount of about 5 to 50 $\mu$l which is usually used in the microanalysis, more preferably 8 to 20 $\mu$l.

As described above, the elements of this invention can be used by contacting them with fluid samples to be analyzed and measuring the concentrations of the detectable products formed within said elements according to various spectrophotometric methods to determine the concentrations of predetermined components in said fluid samples by calculation.

It is possible to prepare various different elements according to this invention, which can be used not only in the field of clinical chemistry but also in various fields of chemical research.

The present invention is further illustrated by referring to the typical embodiments of the invention in comparison with the analytical elements of the prior art, by which this invention is not of course limited.

EXAMPLE 1

On a transparent polyethyleneterephthalate support with a thickness of about 180μ, there were provided: (1) a reagent layer having a thickness of dried film of about 30μ, comprising:

| | |
|---|---|
| Deionized gelatin | 160 mg/dm² |
| Exemplary copolymer (1) or (15) of this invention | 160 mg/dm² |
| 1,7-Dihydroxynaphthalene | 6.60 mg/dm² |
| 4-Aminoantipyrine hydrochloride | 9.70 mg/dm² |
| Glucose oxidase | 244.1 international units/dm² |
| Peroxidase | 248 AAP units/dm² |
| Dimedone | 2.15 mg/dm² |
| 3,3-Dimethylglutaric acid | 19.6 mg/dm² | and (2) a non-fibrous porous spreading layer having a thickness of dried film of about 140μ, comprising:

| | |
|---|---|
| Cellulose acetate | 70.4 mg/dm² |
| Titanium dioxide | 505.9 mg/dm² |
| Octylphenoxypolyethoxyethanol (nonionic surfactant) | 13.8 mg/dm² |
| Polyurethane polymer | 15.5 mg/dm². |

Of the above analytical elements for analysis of glucose, that employing Exemplary copolymer (1) was designated as Analytical Element (I) and that employing Exemplary copolymer (15) as Analytical Element (II).

Further, on the reagent layers as employed in the above Analytical Elements (I) and (II), respectively, there were laminated fibrous porous speading layers each having the following composition, to provide Analytical Elements (III) and (IV), respectively:

(2) a fibrous porous spreading layer having a thickness of dried film of about 160μ, comprising:

| | |
|---|---|
| Powdery filter paper (Toyo Roshi Co., 300 mesh or more) | 910 mg/dm² |
| Copoly(styrene-glycidyl methacrylate) (weight ratio 90:10) | 139 mg/dm² |
| Octylphenoxypolyethoxyethanol (nonionic surfactant) | 31.5 mg/dm² |

On the other hand, as Comparative Analytical Element (I), the water-dispersible copolymer of this invention was replaced with gelatin, while the water-dispersible copolymer of this invention was replaced with the water-dispersible copolymer (methyl acrylate/sodium 3-acryloyloxypropane sulfonate/2-acetoxyethyl acrylate=88.75/4.75/6.5) to provide Comparative Analytical Element (II) [with the spreading layers being nonfibrous porous spreading layers].

The above Analytical Elements (I) through (IV) and Comparative Analytical Elements (I) and (II) were left to stand at 5° C. in a dark place, and at 25° C. in a dark place, for 20 weeks, followed by measurement of reflective densities at 540 nm to determine the degree of deterioration after storage from the difference from the measured value before being left to stand:

$$\Delta(\%) = [(D_R - D_{Ro})/D_{Ro}] \times 100$$

wherein $D_R$ is reflective density at 540 nm after being left to stand for 20 weeks, and $D_{Ro}$ is reflective density at 540 nm before being left to stand.

TABLE 1

| | Dark place, 5° C. 20 weeks | Dark place, 25° C. 20 weeks |
|---|---|---|
| Analytical Element (I) | 8% | 31% |
| Analytical Element (II) | 6.5% | 22% |
| Analytical Element (III) | 5.3% | 18.5% |
| Analytical Element (IV) | 5.0% | 16.9% |
| Comparative Analytical Element (I) | 48% | 82% |
| Comparative Analytical Element (II) | 30% | 43% |

As can be seen from the above results shown in Table 1, the analytical elements of this invention are good with less formation of fogging by standing as compared with the comparative analytical elements.

EXAMPLE 2

Using the Analytical Elements (I) through (IV) of this invention for analysis of glucose and Comparative Analytical Element (II) employed in Example 1, incubation was effected with 10 μl of Control blood serum containing 150 mg/dl, 350 mg/dl and 500 mg/dl of glucose, respectively, at 37° C. for 7 minutes, followed by measurement of the reflective densities at 540 nm.

The results are shown in Table 2.

TABLE 2

| | 150 mg/dl | 350 mg/dl | 500 mg/dl |
|---|---|---|---|
| Analytical Element (I) | 0.613 | 1.092 | 1.255 |
| Analytical Element (II) | 0.573 | 1.139 | 1.346 |
| Analytical Element (III) | 0.605 | 1.099 | 1.244 |
| Analytical Element (IV) | 0.601 | 1.086 | 1.237 |
| Comparative Analytical Element (II) | 0.701 | 1.090 | 1.186 |

As can be seen from the results shown in Table 2, the analytical elements of this invention are higher in color forming density and greater in gradient, indicating higher sensitivity, than the comparative analytical element.

We claim:

1. An analytical element for use in qualitatively and quantitatively analyzing the presence of a component in an aqueous fluid comprising:
   (a) a light-transmissive support;
   (b) a reagent layer comprising at least one layer positioned on one side of said support, said reagent layer comprising:
      (1) at least one reagent reactive with said component to be analyzed;
      (2) a hydrophilic colloid; and
      (3) a substantially water-dispersible copolymer obtained by the copolymerization of at least one copolymerizable monomer, said at least one copolymerizable monomer being water-soluble and having a non-ionizable group in the side chain thereof, and being represented by formula (I):

$$CH_2=\overset{R_1}{\underset{R_2}{C}}-COX-(CHCH_2O)_n R_3 \quad (I)$$

wherein $R_1$ and $R_2$ may be the same or different, and each represent a hydrogen atom or a methyl group; $R_3$ is a hydrogen atom or a mono-valent organic residue; X is an oxygen atom or a divalent organic group represented by the formula $$-\underset{R_4}{N}-;$$

where $R_4$ is a hydrogen atom, an alkyl group or a group represented by the formula: $-(CHCH_2O)_m R_3$, where m is an integer of 2 to 100; and n is an integer of 2 to 100, with at least one copolymerizable hydrophobic monomer; and (c) a porous spreading layer comprising at least one layer positioned on said reagent layer on the side opposite to that of said support.

2. The analytical element of claim 1, wherein the copolymerizable monomer represented by formula [I], is selected from the group consisting of

| | |
|---|---|
| $CH_2=CHCOO-(CH_2CH_2O)_3 H$ | (1) |
| $CH_2=CHCOO-(CH_2CH_2O)_4 H$ | (2) |
| $CH_2=CHCOO-(CH_2CH_2O)_5 H$ | (3) |
| $CH_2=CHCOO-(CH_2CH_2O)_{25}-H$ | (4) |
| $CH_2=CHCOO-(CH_2CH_2O)_{10}-CH_3$ | (5) |
| $CH_2=CHCOO-(CH_2CH_2O)_8 CH_2CH_2CH_2CH_3$ | (6) |
| $CH_2=CHCOO-(CH_2CH_2O)_{20}-\text{Ph}$ | (7) |
| $CH_2=\underset{CH_3}{C}COO-(CH_2CH_2O)_5 H$ | (8) |
| $CH_2=\underset{CH_3}{C}COO-(CH_2CH_2O)_3 H$ | (9) |
| $CH_2=\underset{CH_3}{C}COO-(CH_2CH_2O)_{30}-H$ | (10) |
| $CH_2=\underset{CH_3}{C}COO-(CH_2CH_2O)_{15}-CH_2CH_3$ | (11) |
| $CH_2=\underset{CH_3}{C}COO-(CH_2CH_2O)_{20}-\text{Ph}$ | (12) |
| $CH_2=CHCOO-(\underset{CH_3}{C}HCH_2O)_2 H$ | (13) |
| $CH_2=CHCOO-(\underset{CH_3}{C}HCH_2O)_{10}-H$ | (14) |
| $CH_2=CHCOO-(\underset{CH_3}{C}HCH_2O)_5-\text{Ph}$ | (15) |
| $CH_2=\underset{CH_3}{C}COO-(\underset{CH_3}{C}HCH_2O)_{10}-$ | (16) |
| $CH_2=\underset{CH_3}{C}COO-(\underset{CH_3}{C}HCH_2O)_{15}-H$ | (17) |
| $CH_2=\underset{CH_3}{C}COO-(\underset{CH_3}{C}HCH_2O)_{20}-CH_2CH_2CH_3$ | (18) |
| $CH_2=CHCONH-(CH_2CH_2O)_{10}-H$ | (19) |
| $CH_2=CHCONH-(CH_2CH_2O)_{15}-H$ | (20) |
| $CH_2=CHCONH-(CH_2CH_2O)_5 CH_3$ | (21) |
| $CH_2=CHCON\begin{Bmatrix}-(CH_2CH_2O)_5 H \\ -(CH_2CH_2O)_3 H\end{Bmatrix}$ | (22) |
| $CH_2=\underset{CH_3}{C}CONH-(CH_2CH_2O)_{15}-H$ | (23) |
| $CH_2=\underset{CH_3}{C}CONH-(CH_2CH_2O)_{21}-CH_3$ | (24) | and $$CH_2=\underset{CH_3}{C}-CONH-(\underset{CH_3}{C}HCH_2O)_{30}-H \quad (25)$$

3. The analytical element of claim 1, wherein said copolymerizable hydrophobic monomer is selected from the group consisting of a copolymerizable ethylenically unsaturated nitrile; a styrene; an acrylate; a methacrylate; an acrylamide; a methacrylamide; a vinyl heterocyclic compound; a crosslinkable monomer; a vinyl halide; a vinylidene halide; a vinyl ester; and a conjugated diene.

4. The analytical element of claim 1, wherein said substantially water-dispersible copolymer is selected from the group consisting of $$-(CH_2-CH)_x- \quad -(CH_2-CH)_y- \quad (1)$$
$$\underset{COO-(CH_2CH_2O)_x H}{|} \quad \underset{COOCH_3}{|}$$

x:y = 5:95

$$-(CH_2-CH)_x- \quad -(CH_2-CH)_y- \quad (2)$$
$$\underset{COO-(CH_2CH_2O)_x H}{|} \quad \underset{COOC_4H_9}{|}$$

x:y = 10:90

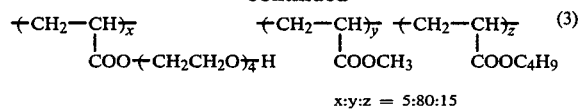
(3) x:y:z = 5:80:15
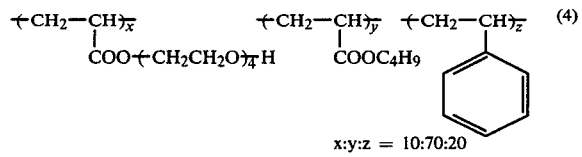
(4) x:y:z = 10:70:20
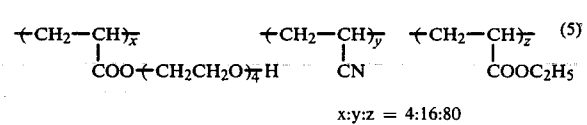
(5) x:y:z = 4:16:80
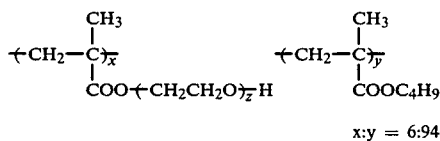
(6) x:y = 6:94
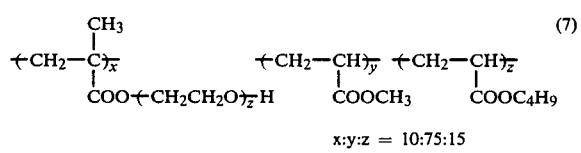
(7) x:y:z = 10:75:15
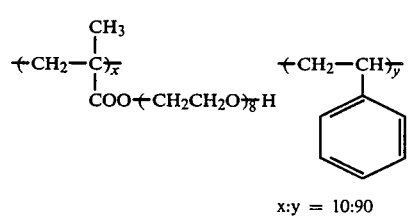
(8) x:y = 10:90
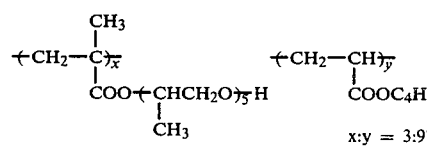
(9) x:y = 3:97
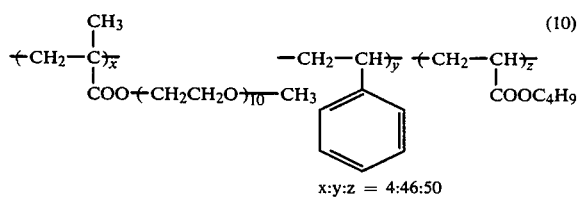
(10) x:y:z = 4:46:50
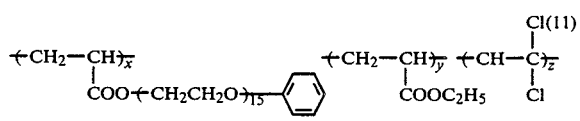
(11) x:y:z = 15:35:50
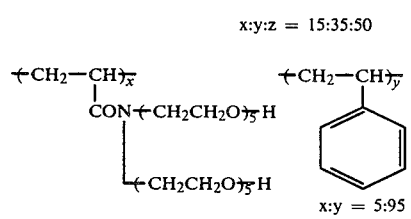
(12) x:y = 5:95
(13) x:y = 3:97
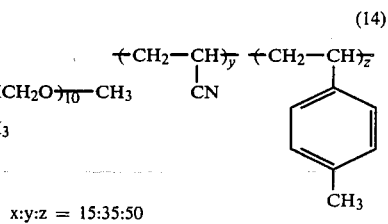
(14) x:y:z = 15:35:50
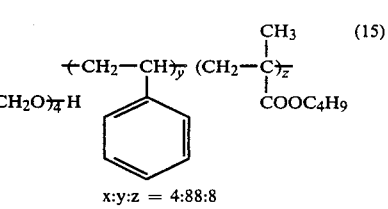
(15) x:y:z = 4:88:8
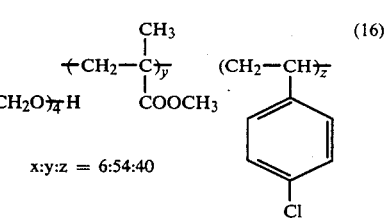
(16) x:y:z = 6:54:40
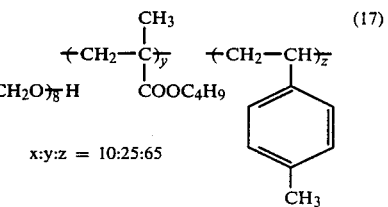
(17) x:y:z = 10:25:65
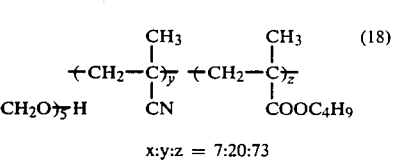
(18) x:y:z = 7:20:73
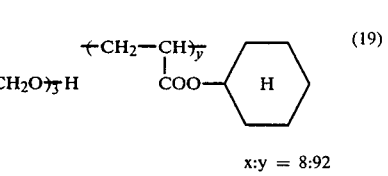
(19) x:y = 8:92
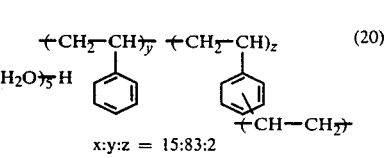
(20) x:y:z = 15:83:2
and -continued

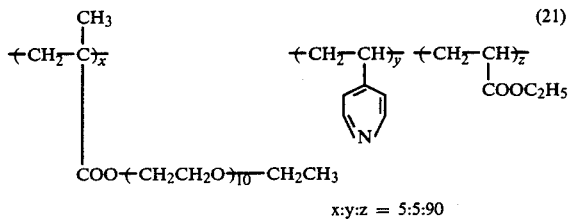

x:y:z = 5:5:90

5. The analytical element of claim 1 wherein said at least one reagent is dispersed or dissolved in said hydrophilic colloid.

6. The analytical element of claim 1 wherein said substantially water dispersible copolymer is present in an amount of between about 5 and 60% by weight based on the weight of said hydrophilic colloid.

7. The analytical element of claim 1 wherein said porous spreading layer is a fibrous porous spreading layer.

8. The analytical element of claim 1 wherein said porous spreading layer is a non-fibrous porous spreading layer.

9. The analytical element of claim 1, wherein said substantially water-dispersible copolymer consists of about 0.5 to about 30% by weight of the copolymerizable monomer represented by formula [I] and about 70 to about 99.5% by weight of the copolymerizable hydrophobic monomer.

10. The analytical element of claim 9, wherein said substantially water-dispersible copolymer consists of about 1.0 to about 20% by weight of the copolymerizable monomer represented by formula [I] and about 80 to about 99% by weight of the copolymerizable hydrophobic monomer.

11. The analytical element of claim 1 wherein said light-transmissive support is impervious to liquids.

12. The analytical element of claim 11 wherein said support has a thickness of between about 50 and 250 microns.

13. The analytical element of claim 11 further comprising a light-transmissive subbing layer between said support and said reagent layer.

* * * * *